United States Patent [19]

Rybicki et al.

[11] 4,011,602
[45] Mar. 15, 1977

[54] POROUS EXPANDABLE DEVICE FOR ATTACHMENT TO BONE TISSUE

[75] Inventors: Edmund F. Rybicki, Worthington, Ohio; Kenneth Ray Wheeler, Richland, Wash.; Lewis E. Hulbert, Columbus, Ohio; Manuel Tom Karagianes, Richland, Wash.; Craig R. Hassler, Columbus, Ohio

[73] Assignee: Battelle Memorial Institute, Columbus, Ohio

[22] Filed: Oct. 6, 1975

[21] Appl. No.: 620,042

[52] U.S. Cl. .................. 3/1.9; 128/92 B; 128/92 C; 32/10 A
[51] Int. Cl.² ............... A61F 1/24; A61C 13/00
[58] Field of Search ............ 3/1, 1.9–1.913; 128/92 C, 92 CA, 92 R, 92 B, 92 BA, 92 BB, 92 BC; 32/10 A

[56] References Cited

UNITED STATES PATENTS

| | | | |
|---|---|---|---|
| 2,397,545 | 4/1946 | Hardinge | 128/92 B |
| 2,699,774 | 1/1955 | Livingston | 128/92 BB |
| 3,708,883 | 1/1974 | Flander | 32/10 A |
| 3,805,302 | 4/1974 | Mathys | 3/1.91 |
| 3,855,638 | 12/1974 | Pilliar | 3/1 |

FOREIGN PATENTS OR APPLICATIONS

| | | | |
|---|---|---|---|
| 1,961,531 | 7/1970 | Germany | 3/1 |
| 540,713 | 3/1956 | Italy | 32/10 A |

*Primary Examiner*—Ronald L. Frinks
*Attorney, Agent, or Firm*—Philip M. Dunson

[57] ABSTRACT

A device for attaching to substantially solid living bone tissue, comprising a body member having an outer surface shaped to fit approximately into an empty space in the tissue and having pores into which the tissue can grow to strengthen the bond between the device and the tissue, and adjustable means for expanding the body member against the tissue to an extent such as to provide a compressive stress capable of maintaining a snug and stable fit and of enhancing the growth of the tissue into the pores in the body member. The expanding means is adjustable to provide a stress between the tissue and the body member in the range of about 150 to 750 psi, typically 150 to 350 psi. Typically the body member comprises an expandable cylindrical portion having at least one radial slit extending longitudinally from a first end to the vicinity of the opposite (second) end thereof, at least one radial slit extending longitudinally from the second end to the vicinity of the first end thereof, and a tapered cylindrical hole extending coaxially from a wider circular opening in the first end to a narrower circular opening communicating with the second end.

2 Claims, 6 Drawing Figures

POROUS EXPANDABLE DEVICE FOR ATTACHMENT TO BONE TISSUE

BACKGROUND

The development of a prosthesis that provides immediate and long term functional reliability is one of the critical areas in orthopaedic and dental research. Clinical progress has been made in this area largely due to the use of a polymeric material to act as a filler between the prosthesis and bone. However, there is a need for improving the reliability of methods for attaching a prostheses to the bone.

One approach to obtaining a reliable method of attachment for prosthetic devices is through the use of porous metals. In vivo studies with various porous metals have demonstrated tissue compatibility (1), (2), (3). The flexibility to vary pore size and density has led to materials with a range of mechanical properties (4). Studies on bone ingrowth into porous metals have demonstrated that good bone to metal interface strengths can be obtained (1), (5).

Although the bone ingrowth and biocompatible properties of porous metals are described in the literature, it has not been demonstrated that porous metal can provide immediate and long term attachment to bone while functioning under load bearing conditions. Development of such a prosthesis requires consideration of the biologic, materials, and mechanics aspects of the problem.

A porous titanium structure called void metal composite (VMC) was developed at Battelle's Pacific Northwest Laboratories (BNW) under the sponsorship of the Battellle Institute Engineering Science Program. Mechanical and biologic characterizations of VMC showed good tissue compatibility and bone ingrowth properties while exhibiting some mechanical properties similar to bone (1), (4). During this same period of time, studies on the healing properties of bone (6) and the load supporting characteristics of intact bones (7) and orthopaedic implants (8) were conducted at Battelle's Columbus Laboratores (BCL) as part of the Battelle Institute Engineering Science Program. The particular porous metal considered here is fabricated from titanium alloy powder (Ti-6A1-4V) that is compacted by a high energy rate process and sinter-bonded. The material utilized in this study was 50 percent dense and contained spherical 460-micron diameter voids. This void size was found to produce better bone ingrowth than the pore sizes that were larger or smaller. The prosthetic implant considered here can have at least two functions. The first is to act as a base for attaching an artificial joint. The second function is to replace a segment of bone that has been lost due to trauma or disease.

The research program has been centered around three critical elements necessary for the development of a successful VMC prosthesis. First, after implantation, the prosthesis must remain stable and have little movement with respect to adjacent bone. Relative movement can cause the implant to become encapsulated and rejected. The second critical element is an environment that enhances bone ingrowth into the porous metal prosthesis. The third element pertains to the load-supporting requirements of long-term stabilization.

During the first year of this study, efforts were concentrated on the second key element, providing an environment that enhances bone ingrowth into the prosthesis. In a previous study (6), it was found that compressive stress influences healing of an osteotomy in rabbit calvaria. Based on this finding, laboratory experiments were designed and carried out to study what effect, if any, compressive stress has on bone ingrowth into the VMC (3). This information was used in the design of the prosthesis to promote good bone ingrowth (9).

Several different device concepts for meeting the requirements of a stable prosthesis were considered. Finite element models were constructed to examine the critical problem of stress interaction at the porous-metal to bone interface. These models showed the complex load distribution path from the bone to the prosthesis and back to the bone again. Based on the results of the finite element analyses and device fabrication and surgical implantation considerations it was decided to select a prosthesis with an expandable intramedullar pin. Specific steps to design and implant the prosthesis were part of the second year's effort and are described below.

Finite element stress analyses of the expandable mandrel prosthesis were done at BCL. Stress distributions were determined for unit bending, twisting, and axial force conditions. These three component-loading conditions can be combined in suitable combinations to determine stresses in the implant for functional loadings due to weight bearing and body movement by the animal. Data to estimate the force applied to the bone were obtained from consideration of a fractured pin in a previous experiment. The force values ranged from 75 to 200 pounds and were in agreement with the force range estimated independently from a stress analysis during the first year's work. A coefficient of friction between the bone and the VMC was estimated to be 0.4 from laboratory measurements conducted at BNW.

In the mathematical model, the bone was idealized as a tube of circular cross section with inside and outside diameters of 0.4 and 0.65 inch, respectively. The finite-element computer program, ASAAS, was used to perform the stress calculations. This program has been implemented during the year at BCL and permitted the treatment of the non-axisymmetric loading conditions of bending and torsion. In the previous year's work, only the axial loading condition could be treated with the finite element stress analysis technique available at the time.

The elastic modulus of the VMC was taken as $0.70 \times 10^6$ psi as in past calculations. Similarly, the bone was taken to have a modulus of $2.5 \times 10^6$ psi longitudinally and $1.25 \times 10^6$ psi in the transverse direction.

The 1.5-inch long prosthesis section was assumed to be attached at its base to an identical section to form a bone segment replacement configuration which could be inserted in a transected femur. Within the interior of the VMC expandable mandrel, a solid pin was modeled to represent the second component of the concept. In the analysis, the pin was assumed to have been perfectly bonded to the bone. The stresses produced by the tightening process were not considered per se in the mathematical analysis. The analysis focused instead on the stresses produced by loading of the bone and prosthesis as a result of animal activity.

The analysis of axial compression, bending, and twist loading shows stresses in the prosthesis region which in general do not exceed those in the untransected bone. Although the actual in vivo loadings on the bone are not known, the resulting analyses and the prosthesis design are based on maximum loading conditions from available data.

REFERENCES

1. Karagianes. M. T., "Porous Metal as a Hard Tissue Substitute", Biomat. Med. Dev., Art. Org., Vol. 1(2), pp 171–181, 1973.
2. Welsh, P. R. et al., "Surgical Implants — The Role of Surface Porosity in Fixation to Bone and Acrylic", Journal of Bone and Joint Surgery, Vol. 53A, July, 1971, pp 963–977.
3. Harth, G. H. et at., "Tissue Compatibility of Porous Metal Structures", paper presented at the 1970 Spring Meeting of the AIME, May 14, 1970, Las Vegas, Nevada.
4. Wheeler, K. R., Marshall, R. P., and Sump, K. R., "Porous Metals as a Hard Tissue Substitute", Part II, Porous Metal Properties, Biomat., Med. Dev., Art. Org., Vol. 1 (2), pp 337–348, 1973.
5. Galante, J. et al., "Sintered Fiber Metal Composites as a Basis for Attachment of Implants to Bone", Journal of Bone and Joint Surgery, Vol. 53A, January, 1971, pp 101–114.
6. Hassler, C. R., Rybicki, E. F., Simonen, F. A., and Weis, E. B., Jr., "Measurements of Healing at an Osteotomy in a Rabbit Calvarium: The Influence of Applied Compressive Stress on Collagen Synthesis and Calcification", *The Journal of Biomechanics*, Vol. 7, pp 545–550.
7. Rybicki, E. F., Simonen, F. A., and Weis, E. B., "On the Mathematical Analysis of Stress in the Human Femur", J. Biomechanics, Vol. 4, pp 203–215, 1972.
8. Rybicki, E. F. et al., "Mathematical and Experimental Studies on the Mechanics of Plated Transverse Fractures", J. Biomechanics, Vol. 7, pp 377–384, 1974.
9. Rybicki, E. F. et al., "The Effects of Compressive Stress on Bone Ingrowth into Porous Metal and its Applications to Prosthesis Design", Proceeding of 27th ACEMB held Oct. 6–10, 1974, in Philadelphia, Pennsylvania, p 489.

SUMMARY

According to this invention, there is provided a device for attaching to substantially solid living tissue, comprising a body member having an outer surface shaped to fit approximately into an empty space in the tissue and having pores into which the tissue can grow to strengthen the bond between the device and the tissue, and adjustable means for expanding the body member against the tissue to an extent such as to provide a compressive stress capable of maintaining a snug and stable fit and of enhancing the growth of the tissue into the pores in the body member. Typically the expanding means is adjustable to provide a stress between the tissue and the body member in the range of about 150 to 750 psi, more commonly in the range of 150 to 350 psi. Typically the composition and shape of the body member are selected such as to be capable of supporting repeated loading at least as great as any that the tissue could support if intact and undamaged, without detriment to the device or to its connection with the tissue.

Typically the body member comprises a cylindrical portion having at least one radial slit extending longitudinally from a first end to the vicinity of the opposite (second) end thereof, at least one radial slit extending longitudinally from the second end to the vicinity of the first end thereof, and a tapered cylindrical hole extending coaxially from a wider circular opening in the first end to a narrower circular opening communicating with the second end. The adjustable means may comprise a cylindrical member having a tapered portion fitting snugly into the tapered hole in the body member at the first end and a narrower portion extending through the second end, and means for controlling its position in the body member. The portion of the cylindrical member extending through the second end of the body member typically is threaded, and the position controlling means comprises a threaded member positioned thereon so as to exert force against the second end.

A typical device includes means for holding the threaded member in a fixed position on the cylindrical member and means for preventing relative rotation between the cylindrical member and the body member. The position holding means may comprise a sleeve member fixedly secured to the body member and having an inner surface so shaped as to surround and to press against the threaded member in such manner as to prevent relative rotation between the threaded member and the body member.

DRAWINGS

DETAILS

Figure 1:
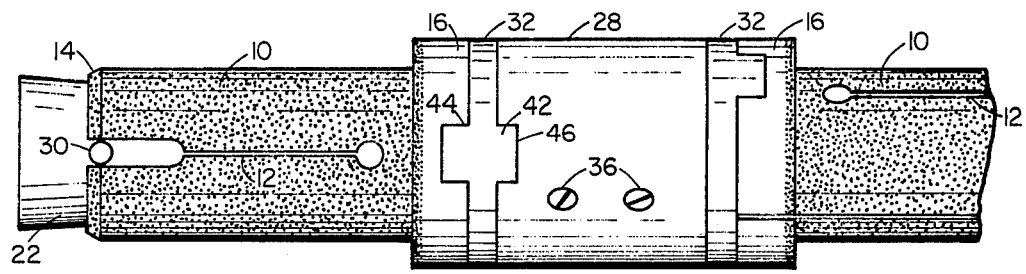
FIG. 1 is a view of an assembled prosthesis in a bone segment replacement configuration which could be inserted in a transected femur. One part has been rotated to better show its details.

Referring to the drawings, there is shown a device for attaching to substantially solid living tissue, such as the bone of a femur or the like. The device comprises a body member 10 having an outer surface shaped to fit approximately into an empty space in the tissue. The outer surface of body member 10 has pores into which the tissue can grow to strengthen the bond between the device and the tissue. It also has adjustable means to be described for expanding the body member 10 against the tissue to an extent such as to provide a compressive stress capable of maintaining a snug and stable fit and of enhancing the growth of the tissue into the pores of the body member.

The expanding means is adjustable to provide a stress between the tissue and the body member 10 in the range of about 150 to 750 psi, or ordinarily in the range of 150 to 350 psi.

The composition and shape of the body member 10 are selected such as to be capable of supporting repeated loading at least as great as any that the tissue could support if intact and undamaged, without detriment to the device or to its connection with the tissue.

Figure 2:
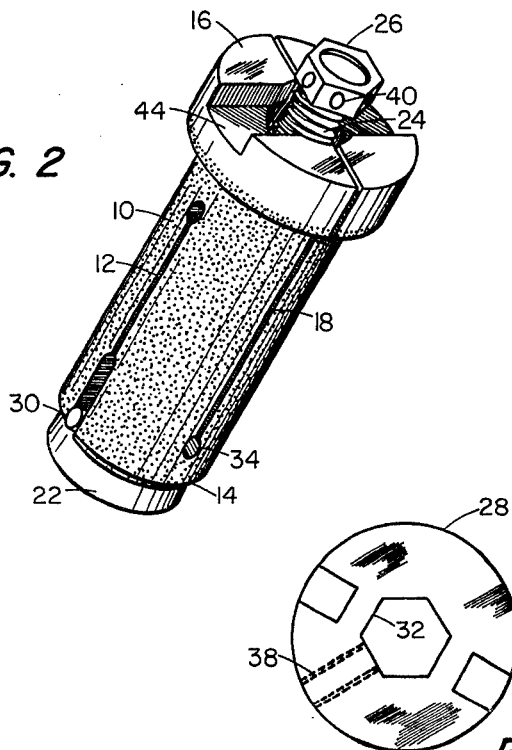
FIG. 2 is an isometric view of one end portion of the device of FIG. 1 with the washer removed to better show the construction of the expandable body member.
Figure 3:
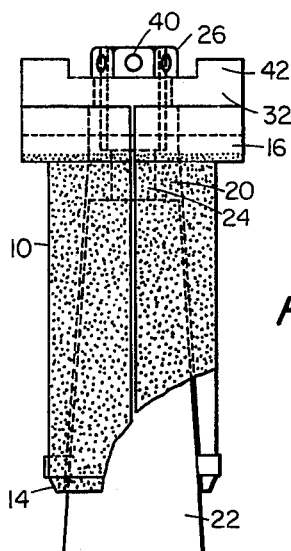
FIG. 3 is an elevational view of an end portion similar to that of FIG. 2, with the washer included and the nut snugly in place.

As shown more particularly in FIGS. 1, 2, and 3, the body member 10 comprises a cylindrical portion having at least one radial slit 12 extending longitudinally from a first end 14 to the vicinity of the opposite (second) end 16 thereof. The body member 10 also has at least one radial slit 18 extending longitudinally from the second end 16 to the vicinity of the first end 14 thereof, and a tapered cylindrical hole 20 extending coaxially from a wider circular opening in the first end 14 to a narrower circular opening communicating with the second end.

The adjustable means comprises a cylindrical member 22 having a tapered portion fitting snugly into the tapered hole 20 in the body member 10 at the first end 14 and a narrower portion 24 extending through the second end 16, and means for controlling its position in the body member. In the device illustrated, the portion 24 of the cylindrical member 22 extending through the second end 16 of the body member 10 is threaded. The position controlling means comprises a threaded member 26 positioned thereon so as to exert force against the second end 16.

The device includes means 28 for holding the threaded member 26 in a fixed position on the cylindrical member and means 30 for preventing relative rotation between the cylindrical member 22 and the body member 10. The position holding means 28 comprises a sleeve member fixedly secured to the body member 10 and having an inner surface 32 so shaped as to surround and to press against the threaded member 26 in such manner as to prevent relative rotation between the threaded member 26 and the body member 10.

A solid washer 32 of material identical to that of the porous cylinder constituting body member 10 is fitted over the second end or T end 16 of the cylinder. The threaded end of the tapered solid pin of the same material which constitutes cylindrical member 22 passes through the washer 32 at a center hole therein. The nut constituting threaded member 26 is screwed onto the threaded portion 24 of the pin 22, and, bearing against the washer 32, draws the tapered solid pin through the tapered porous cylinder in a controlled fashion. As the pin is drawn through the cylinder 10, the cylinder expands diametrically.

The two longitudinal cuts 12 and 18 are made through the cylinder in diametral planes at right angles to each other. Both cuts are terminated into radial holes 34 to remove sharp corners. The number of cuts depends on the cylinder diameter with a minimum required number of 2.

Immediate fixation of the porous-metal device to bone is obtained by the following procedure: the device is inserted into the prepared implant site. The tapered pin 22 is drawn into the expandable porous-metal cylinder 10 by tightening the nut 26, causing the porous cylinder to expand. The cylinder expansion exerts a controlled pressure against the bone surface, immediately and firmly anchoring the device within the implant site. Bone ingrowth into the porous metal eventually provides long-term attachment.

Applications include attaching an artificial joint to a bone or replacing a segment of bone. For the first application, the artificial joint is attached to the T end 16. For the bone segment replacement, one cylinder is inserted in the open end of each bone segment to be joined as shown in FIG. 1. The T ends are connected to span the section of removed bone.

Figure 4:
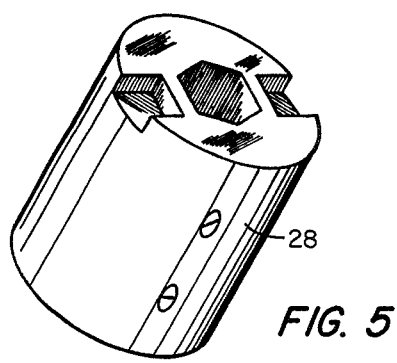
FIG. 4 is an end view of the connecting sleeve of FIG. 1.
Figure 5:
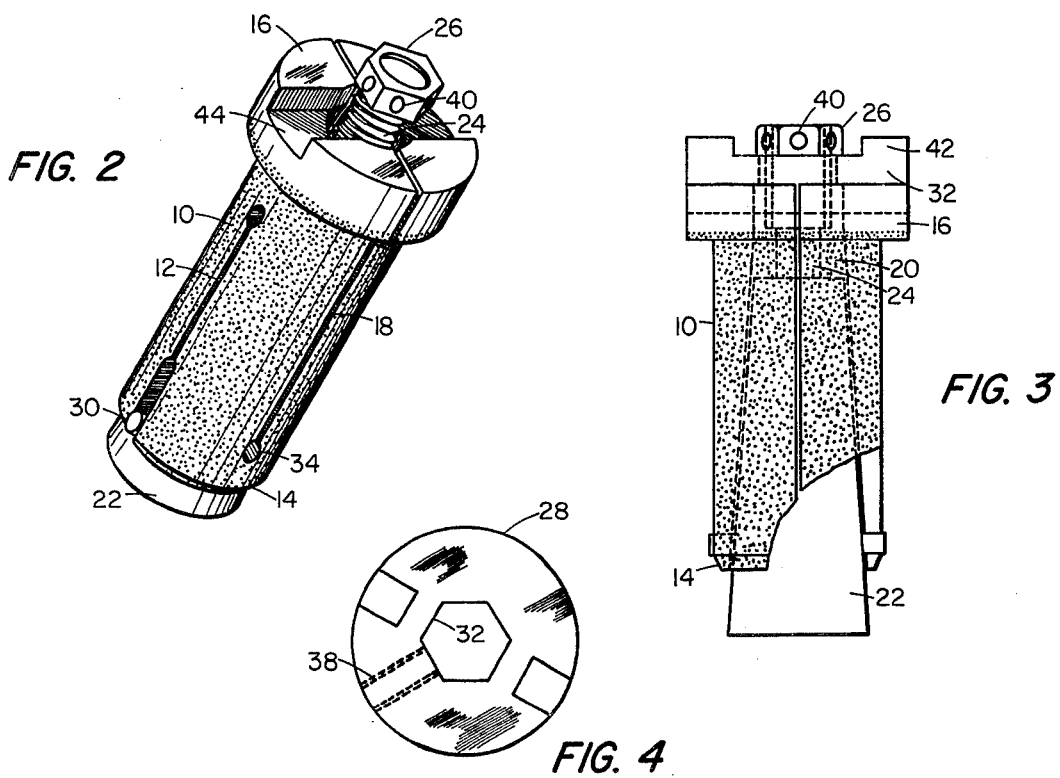
FIG. 5 is an isometric view of the connecting sleeve of FIGS. 1 and 4.
Figure 6:
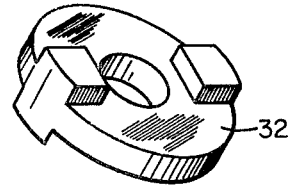
FIG. 6 is an isometric view of one of the washers of FIGS. 1 and 3.

The connection is made using the washers 32, sleeve 28, and set screws 36 which pass through threaded openings 38 in the sleeve 28 as is best shown in FIG. 4. The nut 26 has indentations as at 40 to accommodate the ends of the set screws, so that the coupling can withstand tension even if the set screws should loosen slightly through some mishap.

Relative rotation between the T ends 16 and the sleeve 28 are further prevented by the lugs as at 42 on each side of washers 32, which lugs extend into respective slots 44 and 46 in the T ends and sleeve.

The device, including the porous cylindrical body member 10 is fabricated from the titanium alloy Ti-6A1-4V, and this can be done by the methods described in U.S. Pat. No. 3,852,045.

Laboratory experiments have been carried out to study the effect of bone growth into the void metal composite (VMC). The experiments consisted of implanting transcortical VMC pins in the femora of pygmy goats. Pairs of pins were implanted with a separation between pins of about 1.0 inch. The pins protruded from each side of the bone, and silastic straps were stretched from pin to pin. The silastic straps were calibrated to give known forces.

A finite element stress analysis of the pins loaded by the strap forces was carried out to evaluate the compressive stress at the VMC-bone interface. Unloaded VMC plugs were also implanted to act as controls. Ingrowth after periods of 3 and 6 weeks was studied using mechanical pushout tests and histologic evaluation. The results indicated the existence of an upper stress level (about 750 psi) above which bone ingrowth did not occur. The results also indicted that applied stress levels in the range of 150 to 350 psi produced the maximum pushout stress values presumably indicative of maximum ingrowth within this time period.

We claim:
1. A device for attaching to substantially solid living tissue, comprising
   a body member having an outer surface shaped to fit approximately into an empty space in the tissue and having pores into which the tissue can grow to strenthen the bond between the device and the tissue,
   the body member comprising a cylindrical portion having at least one radial slit extending longitudinally from a first end to the vicinity of the opposite end thereof, at least one radial slit extending longitudinally from the second end to the vicinity of the first end thereof, and a tapered cylindrical hole extending coaxially from a wider circular opening in the first end to a narrower circular opening communicating with the second end,
   adjustable means for expanding the body member against the tissue to an extent such as to provide a compressive stress capable of maintaining a snug and stable fit and of enhancing the growth of the tissue into the pores in the body member,
   the adjustable means comprising a cylindrical member having a tapered portion fitting snugly into the tapered hole in the body member at the first end and a narrower portion extending through the second end, and means for controlling its position in the body member,
   the portion of the cylindrical member extending through the second end of the body member being threaded and the position controlling means com- prising a threaded member positioned thereon so as to exert force against the second end, and means for holding the threaded member in a fixed position on the cylindrical member and means for preventing relative rotation between the cylindrical member and the body member.

2. A device as in claim 1, wherein the position holding means comprises a sleeve member fixedly secured to the body member and having an inner surface so shaped as to surround and to press against the threaded member in such manner as to prevent relative rotation between the threaded member and the body member.

* * * * *